United States Patent
Fujita (10) Patent No.: US 10,634,774 B2
(45) Date of Patent: Apr. 28, 2020

(54) ULTRASOUND DIAGNOSIS APPARATUS AND MEDICAL IMAGE PROCESSING METHOD

(71) Applicant: Toshiba Medical Systems Corporation, Otawara-shi (JP)

(72) Inventor: Tomohiro Fujita, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 520 days.

(21) Appl. No.: 15/402,676

(22) Filed: Jan. 10, 2017

(65) Prior Publication Data

US 2017/0254890 A1    Sep. 7, 2017

(30) Foreign Application Priority Data

Mar. 3, 2016 (JP) ................. 2016-041365

(51) Int. Cl.
| | | |
|---|---|---|
| G01S 7/52 | (2006.01) | |
| A61B 8/14 | (2006.01) | |
| A61B 8/00 | (2006.01) | |
| A61B 8/08 | (2006.01) | |
| G01S 15/89 | (2006.01) | |

(52) U.S. Cl.
CPC .......... *G01S 7/52077* (2013.01); *A61B 8/145* (2013.01); *A61B 8/461* (2013.01); *A61B 8/5269* (2013.01); *G01S 7/52053* (2013.01); *G01S 7/52095* (2013.01); *G01S 15/895* (2013.01)

(58) Field of Classification Search
CPC ............. G01S 7/52077; G01S 7/52053; G01S 15/895; A61B 8/145; A61B 8/461; A61B 8/5269; F01S 7/52095
See application file for complete search history.

(56) References Cited

U.S. PATENT DOCUMENTS

2002/0191742 A1    12/2002  Matsuura

FOREIGN PATENT DOCUMENTS

| JP | 8-308840 A | 11/1996 |
|---|---|---|
| JP | 11-9595 | 1/1999 |
| JP | 2002-344813 | 11/2002 |
| JP | 2014-143497 A | 8/2014 |

OTHER PUBLICATIONS

Office Action dated Oct. 29, 2019 in corresponding Japanese Patent Application No. 2016-041365, 3 pages.

*Primary Examiner* — Lindsey G Wehrheim
(74) *Attorney, Agent, or Firm* — Oblon, McClelland, Maier & Neustadt, L.L.P.

(57) ABSTRACT

According to one embodiment, an ultrasound diagnosis apparatus includes a storage and processing circuitry. The storage is configured to store noise data acquired in advance with respect to each scan line. The processing circuitry is configured to subtract, from raster data sequentially acquired, the noise data corresponding to a scan line of the raster data over a plurality of frames.

13 Claims, 10 Drawing Sheets

ULTRASOUND DIAGNOSIS APPARATUS AND MEDICAL IMAGE PROCESSING METHOD

CROSS-REFERENCE TO RELATED APPLICATION

This application is based upon and claims the benefit of priority from Japanese Patent Application No. 2016-041365, filed Mar. 3, 2016; the entire contents all of which are incorporated herein by reference.

FIELD

Embodiments described herein relate generally to an ultrasound diagnosis apparatus and a medical image processing method.

BACKGROUND

An ultrasound diagnosis apparatus transmits ultrasound waves to a subject using an ultrasound probe, and receives waves reflected therefrom, thereby acquiring biometric information of the subject. The ultrasound diagnosis apparatus generates an ultrasound image that represents, for example, the tissue structure of the subject based on the biometric information.

The ultrasound diagnosis apparatus is provided with a circuit, the miniaturization of which has been being progressed. For example, some ultrasound diagnosis apparatuses are provided with a chip that contains both an analog circuit (e.g., analog-to-digital converter: ADC) for receiving input analog data and a digital circuit (e.g., demodulator) for receiving input digital data. In this case, the behavior of the digital circuit may affect the data in the analog circuit, resulting in occurrence of noise. This noise is sometimes generated periodically, and referred to as "fixed noise".

In conventional technologies, to reduce such noise, received data obtained by transmitting and receiving ultrasound waves as described above and data simply received (noise data) are acquired frame by frame with respect to each scan line. Then, the noise data is subtracted from the received data to reduce the noise. In this case, data is received twice per one scan line. The time required for two times of receiving data twice is an obstacle to maintaining the frame rate. Accordingly, it is difficult to maintain the frame rate as well as reducing noise.

DETAILED DESCRIPTION

In general, according to one embodiment, an ultrasound diagnosis apparatus includes a storage and processing circuitry. The storage is configured to store noise data acquired in advance with respect to each scan line. The processing circuitry is configured to subtract, from raster data sequentially acquired, the noise data corresponding to a scan line of the raster data over a plurality of frames.

Referring now to the drawings, a description is given of an ultrasound diagnosis apparatus and a medical image processing method according to embodiments.

<Embodiment>

Figure 1A:
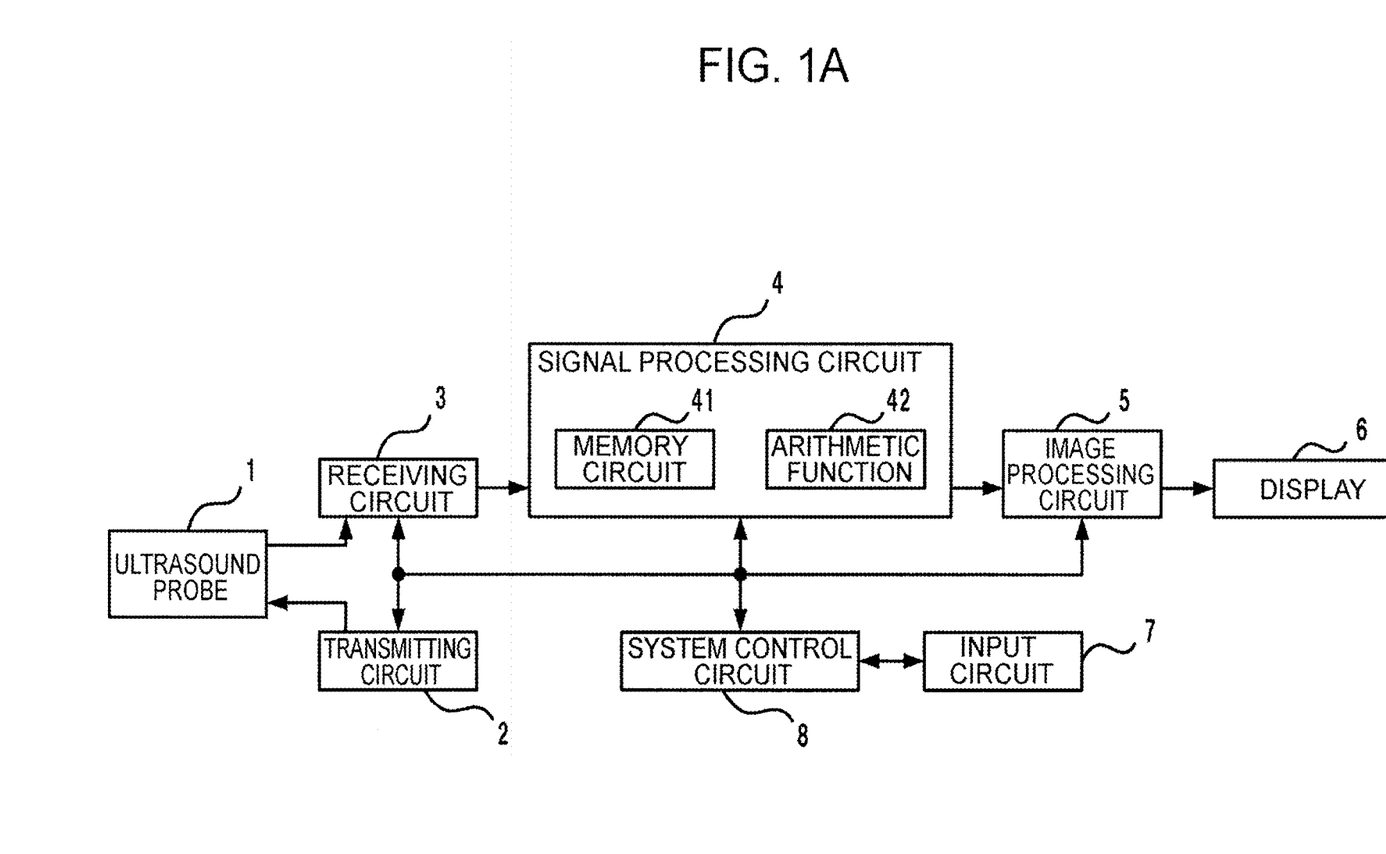
FIG. 1A is a block diagram illustrating the overall configuration of an ultrasound diagnosis apparatus according to an embodiment.

FIG. 1A is a block diagram illustrating the overall configuration of an ultrasound diagnosis apparatus according to an embodiment. According to the embodiment, an ultrasound diagnosis apparatus includes an ultrasound probe 1, a transmitting circuit 2, a receiving circuit 3, a signal processing circuit 4, an image processing circuit 5, a display 6, an input circuit 7, and a system control circuit 8.

[Basic Configuration]

The ultrasound probe 1 transmits ultrasound waves to a subject and receives reflected waves from the subject. The ultrasound probe 1 outputs an echo signal that represents the received reflected waves to the receiving circuit 3. The ultrasound probe 1 is provided with a plurality of ultrasound transducers. As an example of the ultrasound probe 1 may be cited s two-dimensional array probe in which a plurality of ultrasound transducers are arrayed two-dimensionally. Some two-dimensional array probes include thousands of elements of the ultrasound transducers. When there are such a huge number of elements, error may occur in part of the elements in a manufacturing process such as the cutting of the elements of the ultrasound transducers. The element, in which an error has occurred, is likely to cause unnecessary vibration as compared to one-dimensional array probes. As another example of the ultrasound probe 1, a one-dimensional array probe, in which a plurality of ultrasound transducers are arrayed in one row in the scanning direction, may be used.

The transmitting circuit 2 is a processor that outputs a pulse signal to the ultrasound probe 1 to cause it to transmit ultrasound waves. The transmitting circuit 2 includes a pulser for each channel corresponding to each of the ultrasound transducers, and outputs a pulse signal at a timing when delay time is separately assigned to each channel. At this time, in the transmitting circuit 2, a pulser, which corresponds to the ultrasound transducer of the opening channel in the ultrasound probe 1, is driven. Thereby, the transmitting circuit 2 transmits beamformed ultrasound waves (transmitted beam form) to a predetermined focus.

Figure 1B:
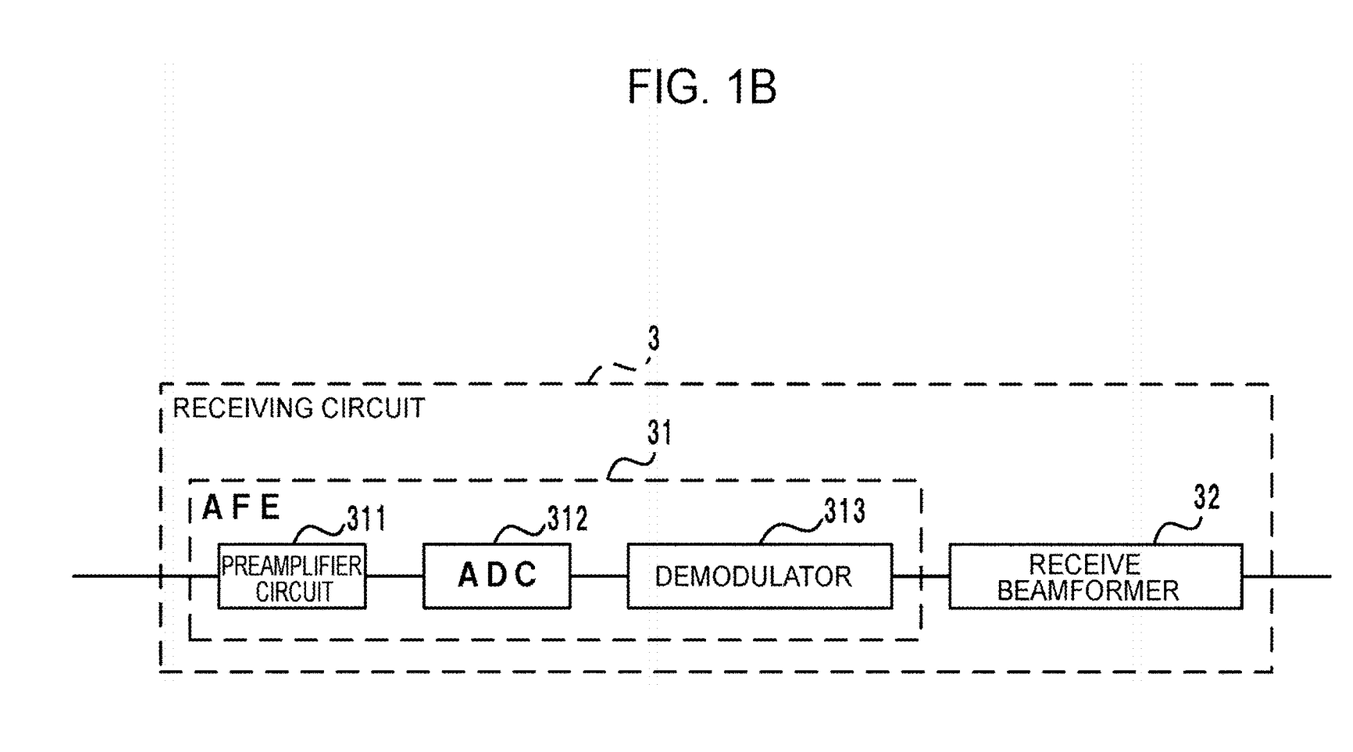
FIG. 1B is a block diagram illustrating the configuration of a receiving circuit of the embodiment.

The receiving circuit 3 is a processor that receives the echo signal from each of the ultrasound transducers of the ultrasound probe 1. FIG. 1B is a block diagram illustrating the configuration of the receiving circuit 3 of the embodiment. The receiving circuit 3 includes a general preamplifier circuit 311, an A/D converter (ADC) 312, a demodulator 313, and a receive phasing delay circuit (receive beamformer 32). Further, as described above, the receiving circuit 3 is provided to an analog front-end (AFE) 31 that is a chip having both analog circuits (the preamplifier circuit 311, the ADC 312) and a digital circuit (the demodulator 313). The preamplifier circuit 311 amplifies the echo signal from the ultrasound probe 1 based on a set gain with respect to each channel, and outputs it to the A/D converter circuit. The A/D converter circuit converts the echo signal amplified by the preamplifier circuit into a digital signal (received signal) for each channel, and outputs it to the demodulator 313. The demodulator 313 decimates received signals based on a determined decimation rate, and outputs to the receive beamformer 32. At this time, the decimation rate can be appropriately set and changed by the operator. For example, when the decimation rate is "4", input data "1024 sample" is thinned to "256 sample". In this case, the demodulator 313 consumes large power once in four times of sample processing. The power consumption may cause periodic fixed noise. The receive beamformer 32 performs phasing and adds delay to the received signal (receive beamforming), and obtains a received beam signal related to a predetermined scan line.

In addition, the receive beamformer 32 obtains amplitude information of the received beam signal. For example, the receive beamformer 32 performs band-pass filtering on the received beam signal, and detects the envelope of the received signal after the band-pass filtering. The receive beamformer 32 performs logarithmic conversion filtering on detected data, and generates ultrasound raster data that represents the tissue image of a subject (hereinafter, referred to as "raster data"). The receive beamformer 32 outputs the raster data to the signal processing circuit 4.

The signal processing circuit 4 includes a memory circuit 41 that stores noise data previously acquired for each scan line, and a processor that subtracts the noise data corresponding to the scan line of raster data, which have been acquired sequentially, from the raster data over a plurality of frames (arithmetic function 42). The details of the signal processing circuit 4 are described later.

The image processing circuit 5 is a processor that generates ultrasound image data based on the raster data, from which fixed noise has been reduced by the signal processing circuit 4. For example, the image processing circuit 5 includes a digital scan converter (DSC). The image processing circuit 5 performs scan conversion of data represented by a signal sequence of the scan line in the raster data into ultrasound image data represented by a coordinate system for display. The image processing circuit 5 generates ultrasound image data (B-mode image data) that represents the tissue image of a subject, and outputs the ultrasound image data to the display 6.

The display 6 displays an ultrasound image based on the ultrasound image data from the image processing circuit 5. The display 6 is formed of, for example, a display device such as a liquid crystal display (LCD) or an organic electroluminescence (EL) display.

In response to an operation performed by an operator such as a doctor or a technician, the input circuit 7 sends a signal corresponding to the content of the operation to the system control circuit 8. The input circuit 7 includes, for example, a track ball, a switch button, a mouse, a keyboard, a touch command screen, a sensitivity time control (STC) slide volume, and the like.

The system control circuit 8 is a processor that implements the functions of each circuit of the ultrasound diagnosis apparatus. The system control circuit 8 stores computer programs in advance and executes them to realize the functions of the circuits.

Figure 2:
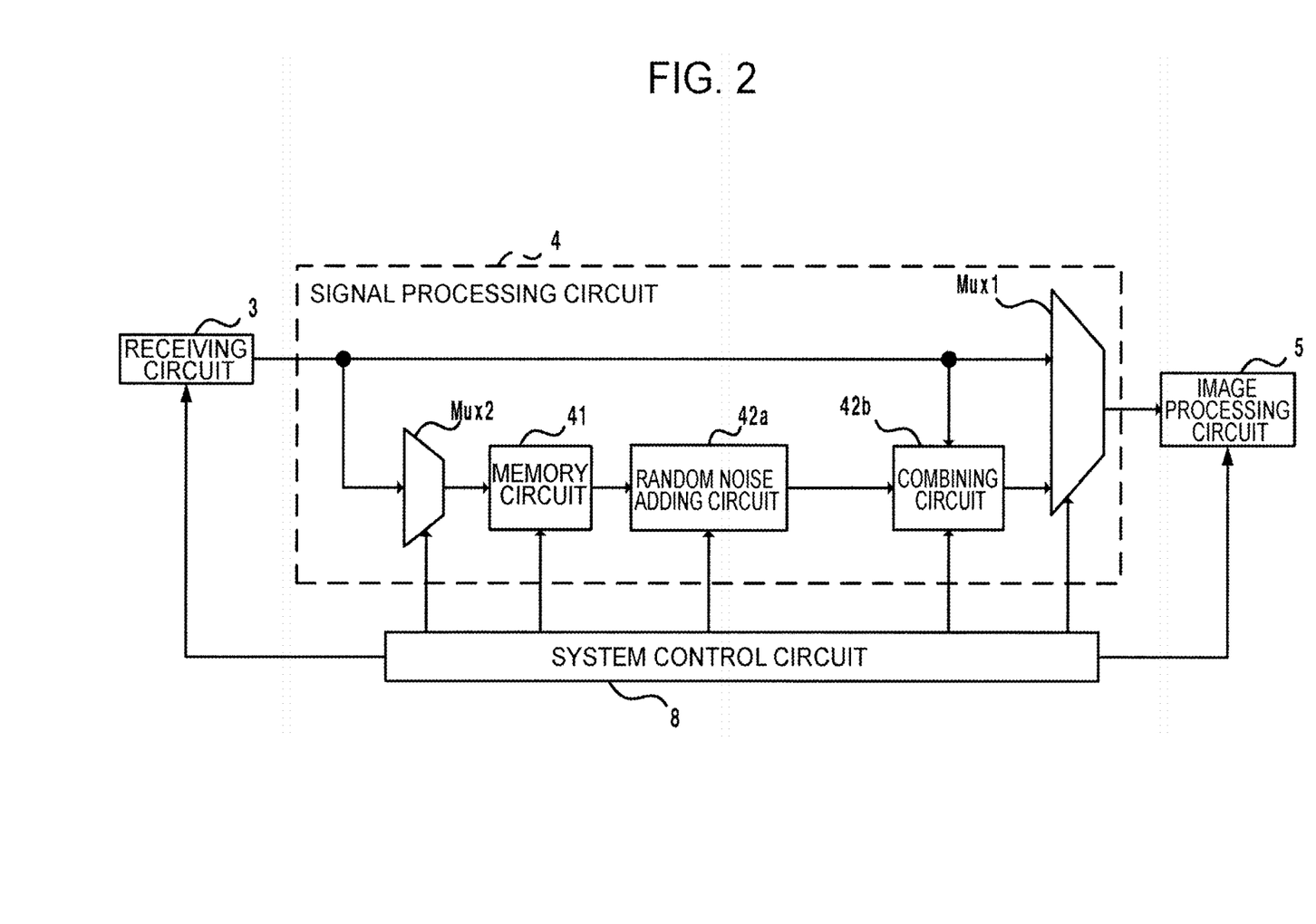
FIG. 2 is a block diagram illustrating the circuit configuration of a signal processing circuit of the embodiment.

Described below is the signal processing circuit 4. FIG. 2 is a circuit block diagram illustrating the circuit configuration of the signal processing circuit 4 of the embodiment. The signal processing circuit 4 of the embodiment includes the memory circuit 41, a random noise adding circuit 42a, a combining circuit 42b, and multiplexers (Mux1, Mux2). Each part of the signal processing circuit 4 is controlled by a control signal from the system control circuit 8.

[Noise Data Acquisition]

First, a description is given of the operation until the memory circuit 41 stores noise data obtained. At this time, the transmitting circuit 2 does not operate. The receiving circuit 3 receives data (noise data) with respect to each scan line in a state where the transmitting circuit 2 does not operate, i.e., a state where the ultrasound probe 1 does not transmit ultrasound waves. The receiving circuit 3 sequentially outputs the noise data to the signal processing circuit 4.

The multiplexer Mux1 is in a state of not passing a signal to the image processing circuit 5 in the subsequent stage according to a control signal from the system control circuit 8. The multiplexer Mux2 is in a state of passing a signal to the memory circuit 41 in the subsequent stage according to a control signal from the system control circuit 8. Thereby, the noise data from the receiving circuit 3 is sent to the memory circuit 41. The memory circuit 41 stores the noise data in a memory address for each scan line based on a control signal from the system control circuit 8. Each piece of the noise data thus stored is data that contains fixed noise in the scan line. The ultrasound diagnosis apparatus of the embodiment stores the noise data in this manner. After that, the ultrasound diagnosis apparatus generates an ultrasound image while reducing the fixed noise.

[Noise Reduction]

Described below is a configuration to reduce fixed noise. At this time, the transmitting circuit 2 is in operation. The transmitting circuit outputs a pulse signal to the ultrasound probe 1 to transmit ultrasound waves. The receiving circuit 3 receives raster data with respect to each scan line in a state where the transmitting circuit 2 is in operation, i.e., a state where the ultrasound probe 1 transmits ultrasound waves and receives the ultrasound waves reflected from the subject. The receiving circuit 3 sequentially outputs the raster data thus acquired to the signal processing circuit 4.

The multiplexer Mux1 is in a state of passing a signal received from the combining circuit 42b to the image processing circuit 5 in the subsequent stage according to a control signal from the system control circuit 8. The multiplexer Mux2 is in a state of not passing a signal to the subsequent stage according to a control signal from the system control circuit 8. As a result, the raster data from the receiving circuit 3 is sent to the combining circuit 42b.

Figure 3:
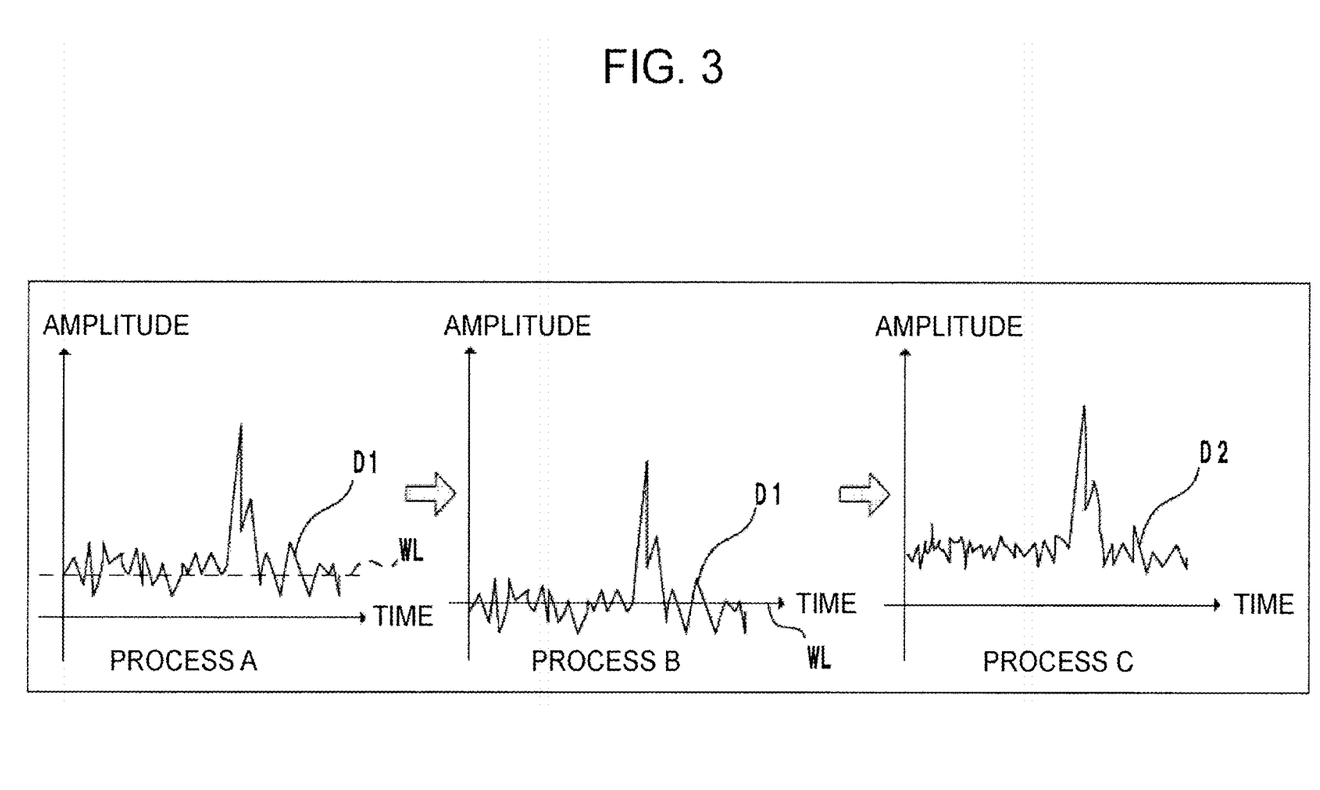
FIG. 3 is a schematic diagram illustrating processes performed in a random noise adding circuit of the embodiment.

The random noise adding circuit 42a adds different random noise data to each piece of the noise data. FIG. 3 is a schematic diagram illustrating processes of the random noise adding circuit 42a of the embodiment. The random noise adding circuit 42a retrieves noise data D1 from the memory address of a predetermined scan line in the memory circuit 41 based on a control signal from the system control circuit 8.

The random noise adding circuit 42a calculates white noise level WL based on the gain of the receiving circuit 3 and the opening channel of the ultrasound probe (process A in FIG. 3). Next, the random noise adding circuit 42a performs lower bit truncation equivalent to the calculated white noise level WL on the noise data D1 (process in FIG. 3 B). Then, the random noise adding circuit 42a generates random noise data of the number of bits truncated. The random noise adding circuit 42a adds the random noise data to the noise data D1 (process C). The data after this is noise data D2 in FIG. 3 (process C). The random noise adding circuit 42a performs the process A to process C for each scan line. How to calculate the white noise level WL, how to truncate lower bits, and how to generate the random noise data are set in advance. The settings of these methods may be changeable by the operator. The random noise adding circuit 42a outputs the noise data D2, to which the random noise data has been added, to the combining circuit 42b.

Figure 4:
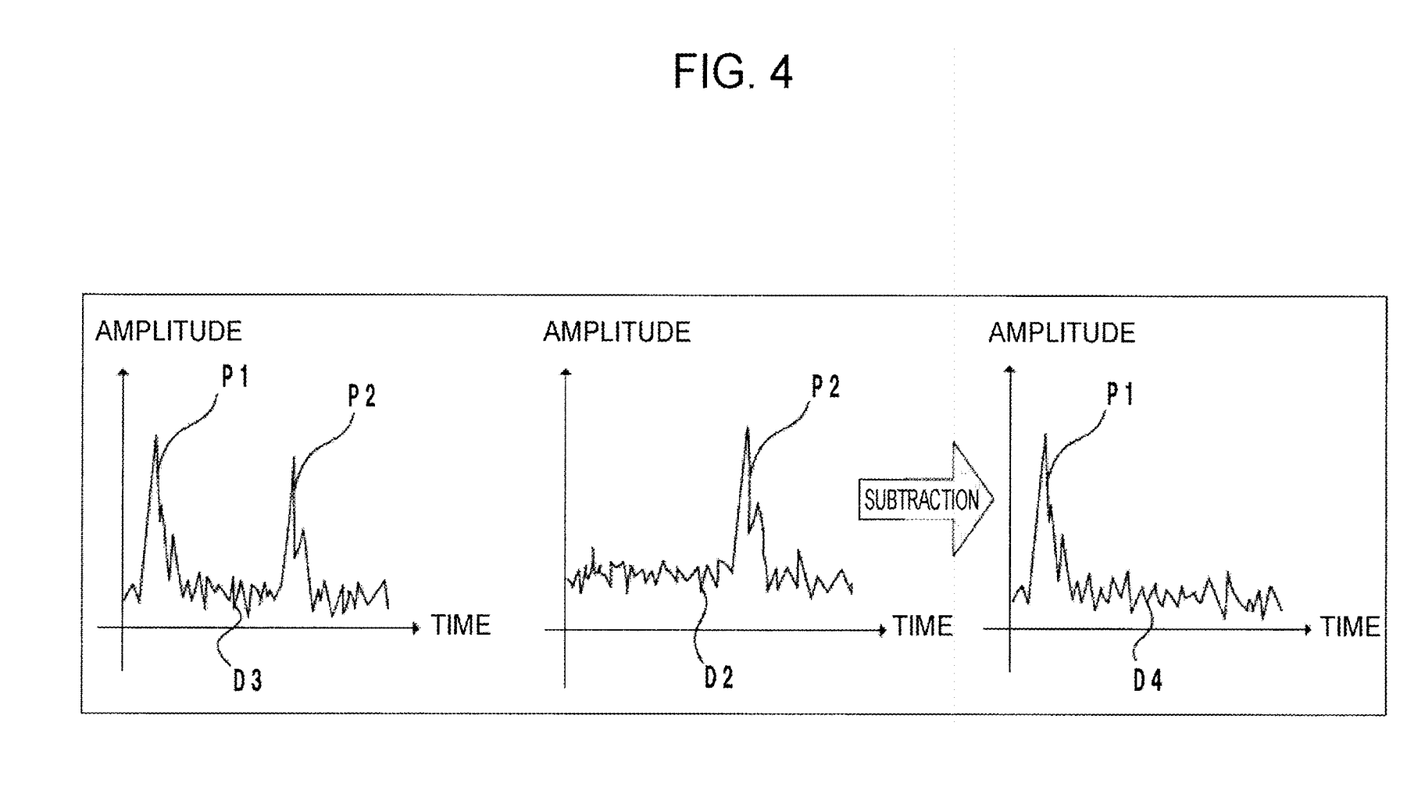
FIG. 4 is a schematic diagram illustrating processes performed in a combining circuit of the embodiment.

The combining circuit 42b subtracts noise data corresponding to the scan line of the raster data from the raster data sequentially acquired. FIG. 4 is a schematic diagram illustrating processes performed in the combining circuit 42b of the embodiment. The combining circuit 42b receives raster data D3 from the receiving circuit 3. The raster data D3 includes partial data P1 valid as an ultrasound image and partial data P2 representing fixed noise in the scan line. The combining circuit 42b receives the noise data D2 from the random noise adding circuit 42a. The noise data D2 indicates fixed noise corresponding to the scan line of the raster data D3. The combining circuit 42b subtracts the noise data D2 from the raster data D3. FIG. 4 illustrates raster data D4, in which the partial data P2 representing fixed noise has been reduced by the subtraction. The combining circuit 42b outputs the raster data D4 to the multiplexer Mux1. The output coefficient at this time is set to "1" (i.e., equal magnification) by the system control circuit 8. The random noise adding circuit 42a and the combining circuit 42b associates the scan lines of the raster data D3 with the scan lines of the noise data D2 based on a control signal from the system control circuit 8. Further, the random noise adding circuit 42a and the combining circuit 42b repeat the noise reduction during the generation of the ultrasound image.

As described above, the multiplexer Mux1 is in a state of passing a signal received from the combining circuit 42b to the image processing circuit 5 in the subsequent stage according to a control signal from the system control circuit 8. Thus, the raster data D4, in which the partial data P2 representing fixed noise has been reduced, is output to the image processing circuit 5. The image processing circuit 5 generates ultrasound image data based on the raster data D4, in which fixed noise has been reduced. Thereby, ultrasound image data with reduced fixed noise is generated.

Figure 5:
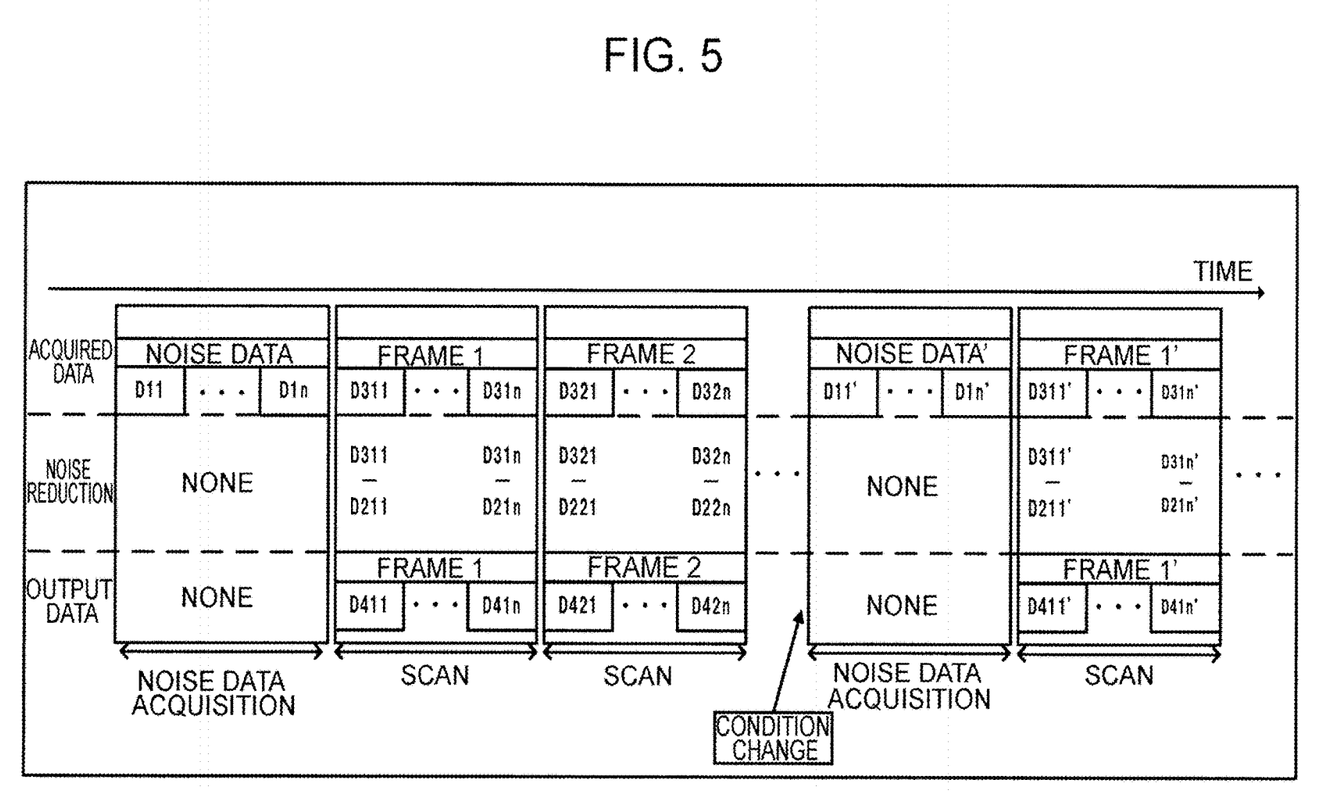
FIG. 5 is a conceptual view of the relationship between noise data acquisition and noise reduction an ultrasound diagnosis apparatus according to a modification of the embodiment.

FIG. 5 is a conceptual view of the relationship between the noise data acquisition and the noise reduction according to the embodiment. The horizontal axis is a time axis indicating the time relationship of these processes. Described here is an example in which one frame (ultrasound image) is generated with n lines of raster data (scan lines).

In the noise data acquisition, raster data in a state where the transmitting circuit 2 does not operate, i.e., noise data D11 to noise data D1n are obtained for each scan line.

After that, scan is started for generating an ultrasound image. Thus, raster data in a state where the transmitting circuit 2 is in operation, the raster data is acquired for each scan line, and the acquisition process is repeated for each frame. FIG. 5 illustrates raster data (D311 . . . D31n) acquired by the first frame (frame 1), and raster data (D321 . . . D32n) acquired by the second frame (frame 2).

The noise reduction is carried out along with scanning. For example, in the noise reduction in the scanning of the first frame (frame 1), random noise is added to the noise data D11 corresponding to the scan line of the raster data D311 to thereby obtain noise data D211 having the addition of random noise. Then, the noise data D211 thus obtained is subtracted from acquired raster data D311. Raster data D411 obtained as the result of the subtraction is output to the image processing circuit 5. This process is also applied to raster data of other scan lines. For example, in the noise reduction related to another scan line, random noise is added to the noise data D1n corresponding to the scan line of the raster data D31n to thereby obtain noise data D21n having the addition of random noise. Then, the noise data D21n thus obtained is subtracted from acquired raster data D31n. Raster data D41n obtained as the result of the subtraction is output to the image processing circuit 5.

Similar process is performed also in the scanning of the next frame (frame 2) and subsequent frames. For example, in the noise reduction in the scanning of the second frame (frame 2), random noise is added to the noise data D11 corresponding to the scan line of the raster data D321 to thereby obtain noise data D221 having the addition of random noise. Then, the noise data D221 thus obtained is subtracted from acquired raster data D311. Raster data D421 obtained as the result of the subtraction is output to the image processing circuit 5. This process is also applied to raster data of other scan lines. For example, in the noise reduction related to another scan line, random noise is added to the noise data D1n corresponding to the scan line of the raster data D32n to thereby obtain noise data D22n having the addition of random noise. Then, the noise data D22n thus obtained is subtracted from acquired raster data D32n. Raster data D42n obtained as the result of the subtraction is output to the image processing circuit 5.

In this manner, with respect to raster data (D311 . . . D31n, D321 . . . D32n, . . . ) obtained by scanning, noise data (D11 to D1n) obtained by the noise data acquisition process and corresponding to the scan line of the raster data is used. For example, the scan lines of the raster data D311 and the raster data D321 and the noise data D11 correspond to one another. Accordingly, the noise data D11 is used in the noise reduction of both the raster data D311 and the raster data D321. However, the noise data D211 and the noise data D221 after the addition of random noise are different in the white noise portion other than the fixed noise (P2 in FIG. 4) due to the adding process. The same applies to raster data of other scan lines. As described above, for raster data having a corresponding scan line over different frames, noise data having a common fixed noise portion and a different white noise portion is used for the subtraction. Thereby, the white noise is rendered as a fixed point on the ultrasound image, and the fixed point can be prevented from being misdiagnosed as a lesion.

In this manner, after the noise data acquisition process, acquired noise data is used in common for corresponding scan lines, and the subtraction process is performed after the addition of random noise. Thereby, it is not required to acquire noise data for each frame in scanning, and the time taken to acquire noise data can be shortened. Thus, it is possible to maintain the frame rate as well as reducing noise.

[Condition Change]

When a predetermined condition is changed, the memory circuit 41 newly stores noise data. Then, the random noise adding circuit 42a and the combining circuit 42b subtracts the newly stored noise data from raster data. The predetermined condition refers to a condition, the change of which may cause a change in the fixed noise and white noise level. The predetermined condition is set in advance. Examples of the predetermined condition include decimation rate, gain, ultrasound probe, receiving central frequency, and the like. A general technique may be applied to the configuration for detecting a change in the predetermined condition. The system control circuit 8 controls each part when the predetermined condition is changed. In FIG. 5, a portion after "condition change" is a portion that represents the concept when the predetermined condition is changed. After "condition change", new noise data is acquired and stored. New noise data (D11' to D1n') is used in scanning and the noise reduction. Thereby, even when there is a change in the fixed noise and white noise level during the acquisition of an ultrasound image, it is possible to maintain the frame rate as well as reducing noise.

The term "processor" as used herein refers to a circuit such as, for example, central processing unit (CPU), graphics processing unit (GPU), application specific integrated circuit (ASIC), programmable logic device such as simple programmable logic device (SPLD) and complex programmable logic device (CPLD), field programmable gate array (FPGA), and the like. The processor reads programs stored in the memory and executes them, thereby implementing the functions. Instead of storing the programs in the memory, the programs may be directly incorporated into the circuitry of the processor. In this case, the processor reads the programs incorporated into the circuit and executes them to realize the functions. Each processor of the embodiment need not necessarily be configured as a single circuit for each processor, but may be configured as a single processor by combining a plurality of independent circuits. Further, a plurality of constituent elements of the embodiment may be combined into a single processor to implement the functions.

Figure 6:
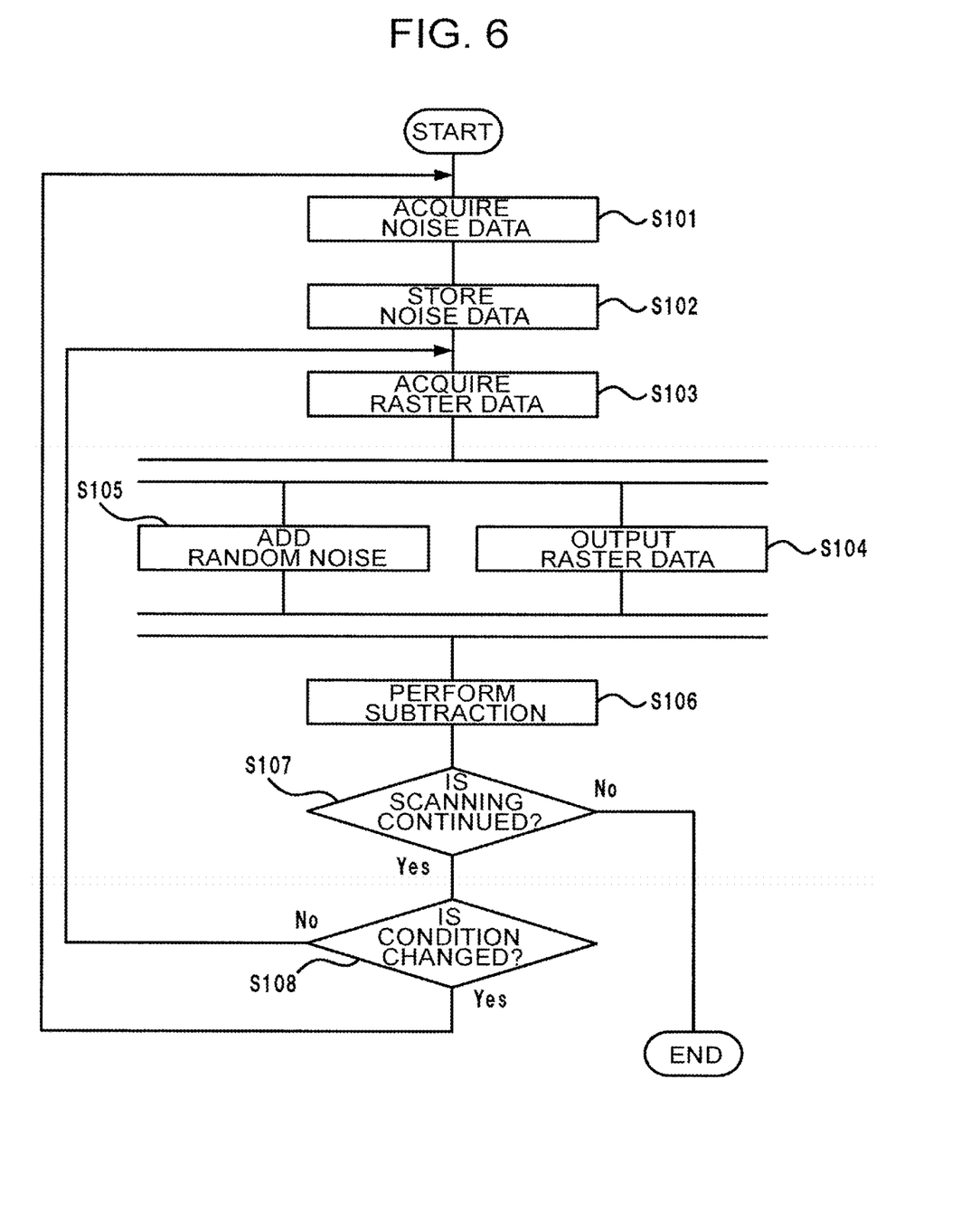
FIG. 6 is a flowchart illustrating the operation of the ultrasound diagnosis apparatus of the embodiment.

FIG. 6 is a flowchart illustrating the operation of the ultrasound diagnosis apparatus according to the embodiment. For example, the system control circuit 8 stores a program corresponding to the medical image processing method that implements the following operation.

Step S101: For example, Step S101 is a step that can be implemented by executing a predetermined program under the control of the system control circuit 8. The receiving circuit 3 acquires data (noise data) with respect to each scan line in a state where the transmitting circuit 2 does not operate, i.e., a state where the ultrasound probe 1 does not transmit ultrasound waves.

Step S102: For example, Step S102 is a step that can be implemented by executing a predetermined program under the control of the system control circuit 8. The noise data is sent to the memory circuit 41. The memory circuit 41 stores the noise data in a memory address for each scan line based on a control signal from the system control circuit 8.

Step S103: The transmitting circuit 2 outputs a pulse signal to the ultrasound probe 1 to cause it to transmit ultrasound waves. The receiving circuit 3 acquires raster data with respect to each scan line in a state where the transmitting circuit 2 is in operation, i.e., a state where the ultrasound probe 1 transmits ultrasound waves and receives the ultrasound waves reflected from the subject. The receiving circuit sequentially outputs the raster data thus acquired to the signal processing circuit 4.

Step S104: The multiplexer Mux1 is in a state of passing a signal received from the combining circuit 42b to the image processing circuit 5 in the subsequent stage according to a control signal from the system control circuit 8. The multiplexer Mux2 is in a state of not passing a signal to the subsequent stage according to a control signal from the system control circuit 8. As a result, the raster data from the receiving circuit 3 is sent to the combining circuit 42b.

Step S105: The random noise adding circuit 42a retrieves noise data D1 from the memory address of a predetermined scan line in the memory circuit 41 based on a control signal from the system control circuit 8. The random noise adding circuit 42a calculates the white noise level WL based on the gain of the receiving circuit 3 and the opening channel of the ultrasound probe (process A in FIG. 3). Next, the random noise adding circuit 42a performs lower bit truncation equivalent to the calculated white noise level WL on the noise data D1. Then, the random noise adding circuit 42a generates random noise data of the number of bits truncated. The random noise adding circuit 42a adds the generated random noise data to the noise data D1.

FIG. 6 illustrates steps S104 and S105 as being performed in parallel. However, if the combining circuit 42b can calculate the raster data D3 and noise data D2, the scan lines of which correspond to each other, in following step S106, steps S104 and S105 may be performed serially.

Step S106: For example, Step S106 is a step that can be implemented by executing a predetermined program under the control of the system control circuit 8. The combining circuit 42b subtracts noise data corresponding to the scan line of the raster data from the raster data sequentially acquired. The combining circuit 42b receives the raster data D3 from the receiving circuit 3. The combining circuit 42b receives the noise data D2 from the random noise adding circuit 42a. The combining circuit 42b subtracts the noise data D2 from the raster data D3. The combining circuit 42b outputs the raster data D4 obtained by the subtraction to the multiplexer Mux1. The multiplexer Mux1 is in a state of passing a signal received from the combining circuit 42b to the image processing circuit 5 in the subsequent stage according to a control signal from the system control circuit 8. Thus, the raster data D4, in which the partial data P2 representing fixed noise has been reduced, is output to the image processing circuit 5.

Step S107: When scanning is continued, i.e., the generation of ultrasound images is continued (Yes in step S107), the operation of the ultrasound diagnosis apparatus of the embodiment proceeds to step S108. When scanning is not continued, i.e., the generation of ultrasound images is not continued (No in step S107), the operation of the ultrasound diagnosis apparatus of embodiment is completed.

Step S108: When a predetermined condition is changed (Yes in step S108), the operation of the ultrasound diagnosis apparatus of the embodiment returns to step S101. Then, new noise data is acquired and stored. When the predetermined condition is not changed (No in step S108), the operation of the ultrasound diagnosis apparatus of the embodiment returns to step S103. Then, raster data for the next scan line of the frame or the first scan line of the next frame is acquired.

With the ultrasound diagnosis apparatus of the embodiment, after the noise data acquisition process in Step S10, acquired noise data is used in common for corresponding scan lines over a plurality of frames, and the subtraction process is performed after the addition of random noise. Thereby, it is not required to acquire noise data for each frame in scanning, and the time taken to acquire noise data can be shortened. Thus, it is possible to maintain the frame rate as well as reducing noise.

Note that, in a two-dimensional array probe cited in the description of the basic configuration of the embodiment, ultrasound waves are transmitted and received (scanned) in multiple directions to obtain volume data of the subject. This increases scan lines per frame. As the number of scan lines per frame is increased, it is more difficult to maintain a high frame rate. Besides, in the conventional method of reducing noise, in which received data obtained by transmitting and receiving ultrasound waves and data simply received (noise data) are acquired frame by frame with respect to each scan line, and the noise data is subtracted from the received data to reduce the noise, the two-dimensional array probe receives data twice per one scan line of volume scanning. Because of the time taken to receive data twice per one scan line of one frame in volume scanning, it has not been possible to keep the frame rate required for diagnosis by volume scanning. On the other hand, according to the embodiment, the noise reduction is more advantageous in the case of using a two-dimensional array probe.

As in the embodiment, if noise data is acquired before the start of sending and receiving (scanning) ultrasound waves, and used over a plurality of frames, acquisition of noise data has already been completed when the ultrasound probe is placed on the body surface of the subject. Besides, according to the embodiment, there is no need to acquire noise data each time at a timing between frames during scanning (e.g., a frame rate of 60 fps, etc.). Further, according to the embodiment, when a predetermined condition described above is changed, scanning is started again after noise data is newly acquired. In this case, the time required to acquire the noise data is the time taken for receiving only (not transmitting ultrasound waves). Thus, the required time is shorter than the time required per scan frame. Accordingly, ultrasound diagnosis can be performed while the frame rate is prevented from falling due to noise data acquisition.

<Modification>

Figure 7:
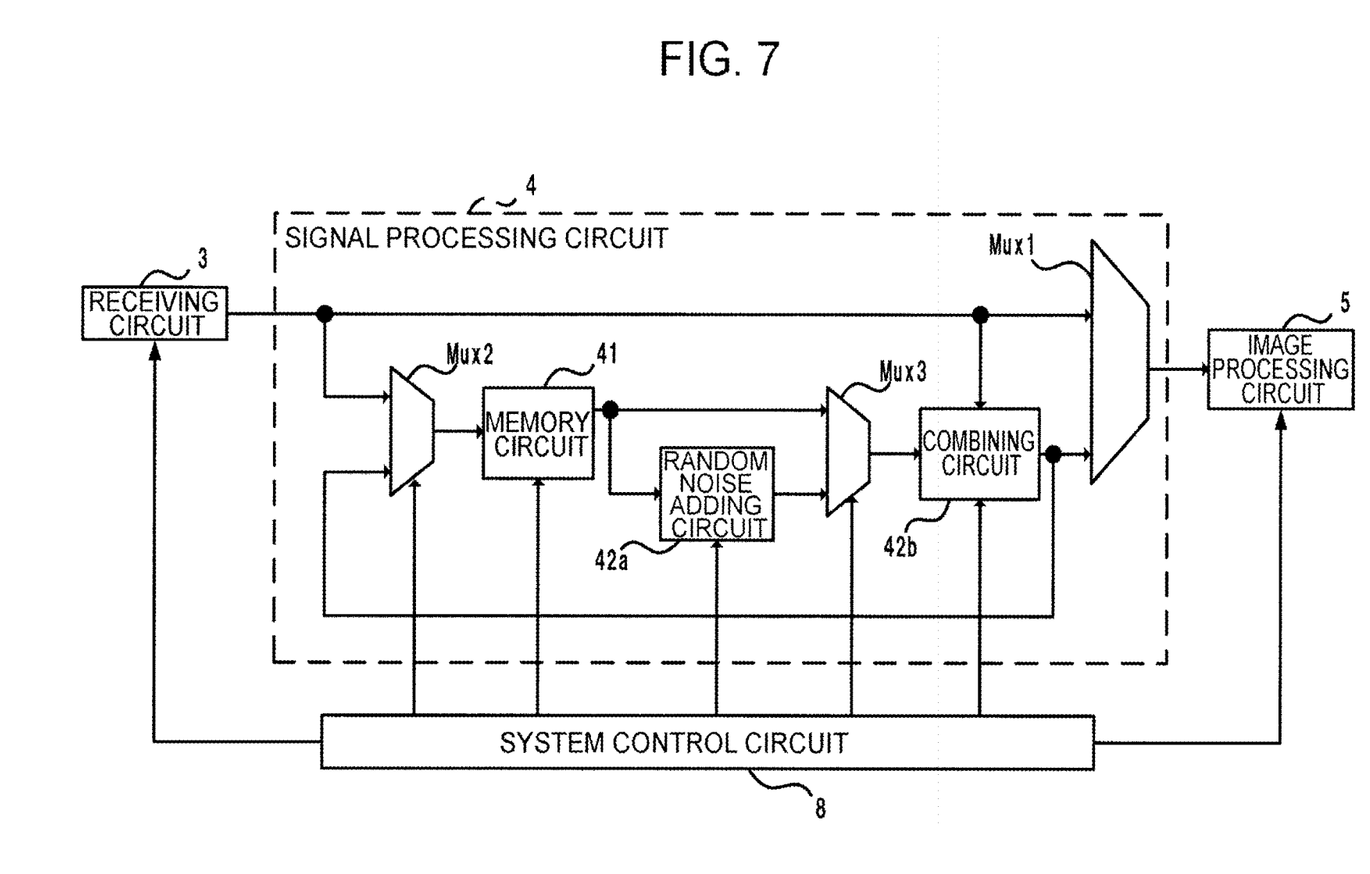
FIG. 7 is a block diagram illustrating the circuit configuration of a signal processing circuit according to a modification.

An ultrasound diagnosis apparatus according to a modification is basically similar to that of the above embodiment except the configuration of the signal processing circuit 4. FIG. 7 is a block diagram illustrating the circuit configuration of the signal processing circuit 4 of the modification. In the following, differences from the ultrasound diagnosis apparatus of the embodiment are mainly described.

In ultrasound diagnosis, for example, a technique called beam combining (raster data synthesis) is sometimes used to produce an ultrasound image of a site with less motion (liver, blood vessels, etc.). In the beam combining, a plurality of pieces of raster data are combined with corresponding scan lines to generate a single image frame. This is known as improving the S/N ratio of the raster data combined. Besides, the beam combining is sometimes performed in the pulse inversion method for extracting a harmonic component. According to the pulse inversion method, for example, the phase of an ultrasound pulse applied to both electrodes of an ultrasound transducer are shifted by 180 degrees (by changing the polarity) and transmitted twice. Then, two echo signals are added and only harmonic component is extracted to form an image. More specifically, pulsers are each connected to each of the poles (front and back electrodes) of the ultrasound transducer so that the pulsers operate alternately to thereby output bipolar pulse. By reversing the order of the alternate operation in two times of transmission, it is possible to output an ultrasound pulse according to the bipolar pulse with a waveform having good positive-negative symmetry in the first transmission and the second transmission. Thus, it is possible to generate a harmonic imaging image.

[Noise Data Acquisition]

In the ultrasound diagnosis apparatus of this modification, the memory circuit 41 stores sum data of pieces of noise data in a number corresponding to the number of pieces of raster data to be combined. This configuration is described below. The receiving circuit 3 receives noise data with respect to each scan line. The receiving circuit 3 sequentially outputs the noise data to the signal processing circuit 4. This process is repeated until a predetermined number of pieces of noise data to be combined are acquired per one scan line (the number of pieces of data to be combined is hereinafter referred to as "combined number").

When the first noise data per one scan line is sent to the signal processing circuit 4, the multiplexer Mux1 is in a state of not passing a signal to the image processing circuit 5 in the subsequent stage according to a control signal from the system control circuit 8. On the other hand, the multiplexer Mux2 is in a state of passing a signal to the memory circuit 41 in the subsequent stage according to a control signal from the system control circuit 8. Further, a multiplexer Mux3 is in a state of not passing a signal to the combining circuit 42*b* in the subsequent stage according to a control signal from the system control circuit 8. Thereby, the first noise data per one scan line is stored in the memory circuit 41. At this time, the memory circuit 41 stores the noise data in a memory address for each scan line based on a control signal from the system control circuit 8.

When the second and subsequent noise data per scan line are sent to the signal processing circuit 4, the multiplexer Mux1 is in a state of not passing a signal to the image processing circuit 5 in the subsequent stage according to a control signal from the system control circuit 8. On the other hand, the multiplexer Mux2 is in a state of passing a signal to the memory circuit 41 in the subsequent stage according to a control signal from the system control circuit 8. Further, the multiplexer Mux3 is in a state of passing a signal from the memory circuit 41 in the preceding stage to the combining circuit 42*b* in the subsequent stage according to a control signal from the system control circuit 8. Thereby, the noise data from the memory circuit 41 and the noise data from the receiving circuit 3 are sent to the combining circuit 42*b*.

The combining circuit 42*b* adds these pieces of noise data based on a control signal from the system control circuit 8. The combining circuit 42*b* outputs the noise data after the addition. The output coefficient at this time is set each time so that the system control circuit 8 outputs average sum data of pieces of noise data in a combined number ("1/2" or the like, the output coefficient is set each time according to the number of sum data at the time of output). Because of the state of the multiplexers Mux1 and Mux2 as described above, the memory circuit 41 stores the noise data output from the combining circuit 42*b*. The combining circuit 42*b* repeats this process until a predetermined number of pieces of noise data to be combined are acquired per one scan line. Thereby, the memory circuit 41 can store average sum data (referred to as "average sum noise data") of noise data in a combined number with respect to each scan line.

[Noise Reduction]

Described below is a configuration in which fixed noise is reduced. The receiving circuit 3 receives raster data with respect to each scan line. The receiving circuit 3 sequentially outputs the raster data thus acquired to the signal processing circuit 4. This process is repeated until a predetermined number of pieces of raster data to be combined are acquired per one scan line.

When the first raster data per one scan line is sent to the signal processing circuit 4, the multiplexer Mux1 is in a state of not passing a signal to the image processing circuit 5 in the subsequent stage according to a control signal from the system control circuit 8. On the other hand, the multiplexer Mux2 is in a state of passing a signal from the combining circuit 42*b* in the preceding stage to the memory circuit 41 in the subsequent stage according to a control signal from the system control circuit 8. Further, a multiplexer Mux3 is in a state of not passing a signal from the random noise adding circuit 42*a* in the preceding stage to the combining circuit 42*b* in the subsequent stage according to a control signal from the system control circuit 8.

The random noise adding circuit 42*a* reads out the average sum noise data stored in the memory circuit 41, and performs the same process as in the above embodiment. Thereby, average sum noise data, to which raster data from the receiving circuit 3 and random noise data have been added, is sent to the combining circuit 42*b*. The combining circuit 42*b* subtracts the average sum noise data from the raster data. The combining circuit 42*b* outputs the raster data obtained by the subtraction. Because of the state of the multiplexers as described above, the memory circuit 41 stores the raster data output from the combining circuit 42*b*.

When each of the second and subsequent raster data (the number of pieces of data to be combined–1) per scan line is sent to the signal processing circuit 4, the multiplexer Mux1 is in a state of not passing a signal to the image processing circuit 5 in the subsequent stage according to a control signal from the system control circuit 8. On the other hand, the multiplexer Mux2 is in a state of passing a signal to the memory circuit 41 in the subsequent stage according to a control signal from the system control circuit 8. Further, the multiplexer Mux3 is in a state of passing a signal from the memory circuit 41 in the preceding stage to the combining circuit 42*b* in the subsequent stage according to a control signal from the system control circuit 8. Thereby, the raster data from the memory circuit 41 and the raster data from the receiving circuit 3 are sent to the combining circuit 42*b*. The combining circuit 42*b* adds up these pieces of raster data. The combining circuit 42*b* outputs the raster data after the addition. Because of the state of the multiplexers as described above, the memory circuit 41 stores the raster data output from the combining circuit 42*b*.

When the last one of a predetermined number of pieces of raster data to be combined per one scan line is sent to the signal processing circuit 4, the multiplexer Mux1 is in a state of passing a signal received from the combining circuit 42*b* in the preceding stage to the image processing circuit 5 in the subsequent stage according to a control signal from the system control circuit 8. On the other hand, the multiplexer Mux2 is in a state of not passing a signal according to a control signal from the system control circuit 8. Further, the multiplexer Mux3 is in a state of passing a signal from the memory circuit 41 in the preceding stage to the combining circuit 42*b* in the subsequent stage according to a control signal from the system control circuit 8. Thereby, the raster data from the memory circuit 41 and the raster data from the receiving circuit 3 (the last one of the combined number) are sent to the combining circuit 42*b*. The combining circuit 42*b* adds up these pieces of raster data. As a result of this addition, the noise data in the combined number are reduced (subtracted) from the raster data in the combined number. The combining circuit 42*b* outputs the raster data after the addition. Because of the state of the multiplexers as described above, the raster data output from the combining circuit 42*b* is sent to the image processing circuit 5.

The ultrasound diagnosis apparatus of the modification has basically a similar configuration to that of the above embodiment except the foregoing. According to the modification, the ultrasound diagnosis apparatus can maintain the frame rate as well as reducing noise even when generating an ultrasound image while performing beam combining.

The memory circuit 41 in the embodiment and the modification described above is an example of a storage in the appended claims. Further, the arithmetic function 42, the random noise adding circuit 42*a*, and the combining circuit 42*b* in the embodiment and the modification described above are examples of the processing circuitry in the claims.

Figure 8A:
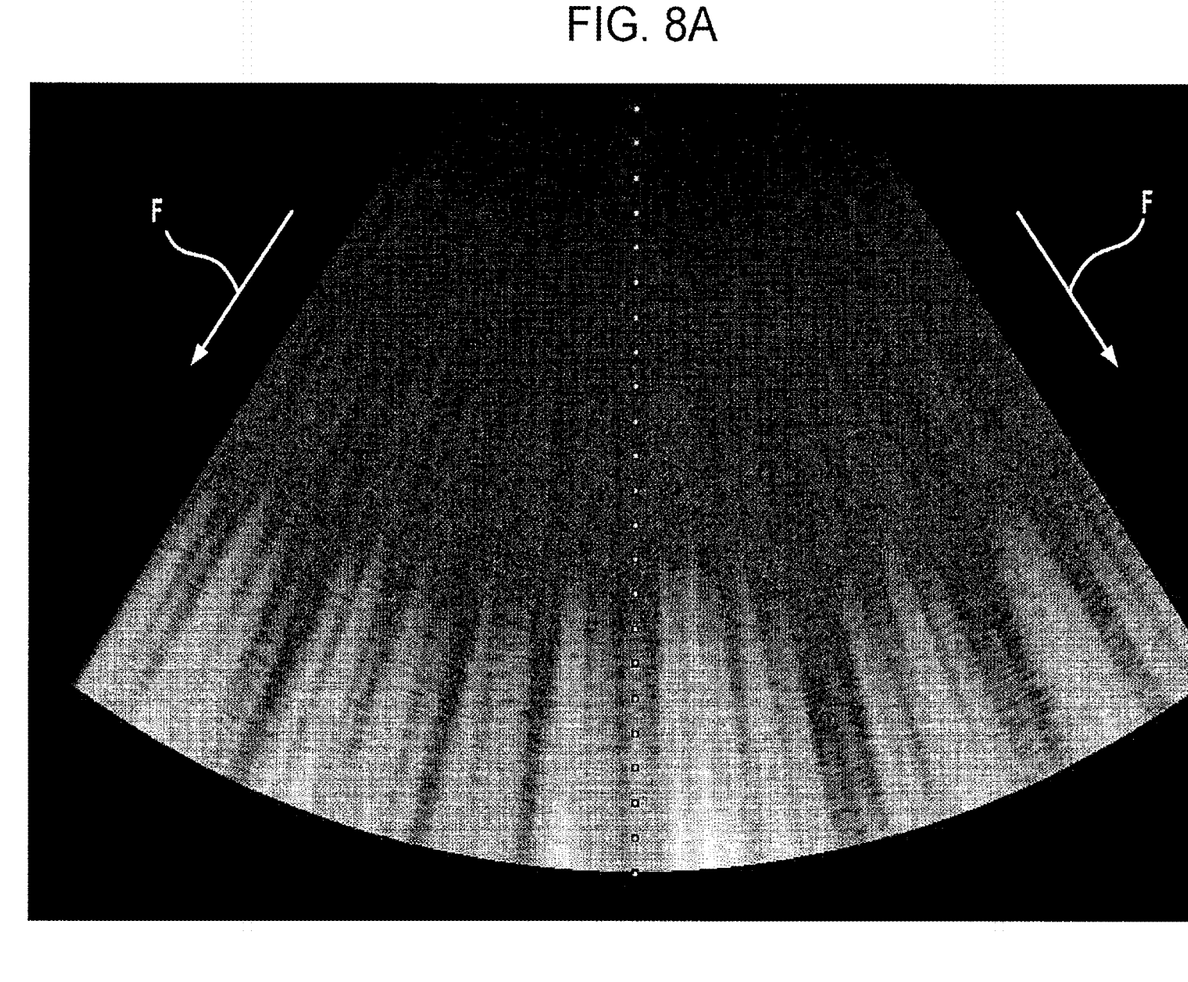
FIG. 8A is a diagram illustrating an example of an ultrasound image captured when the noise reduction is OFF in the embodiment and the modification.
Figure 8B:
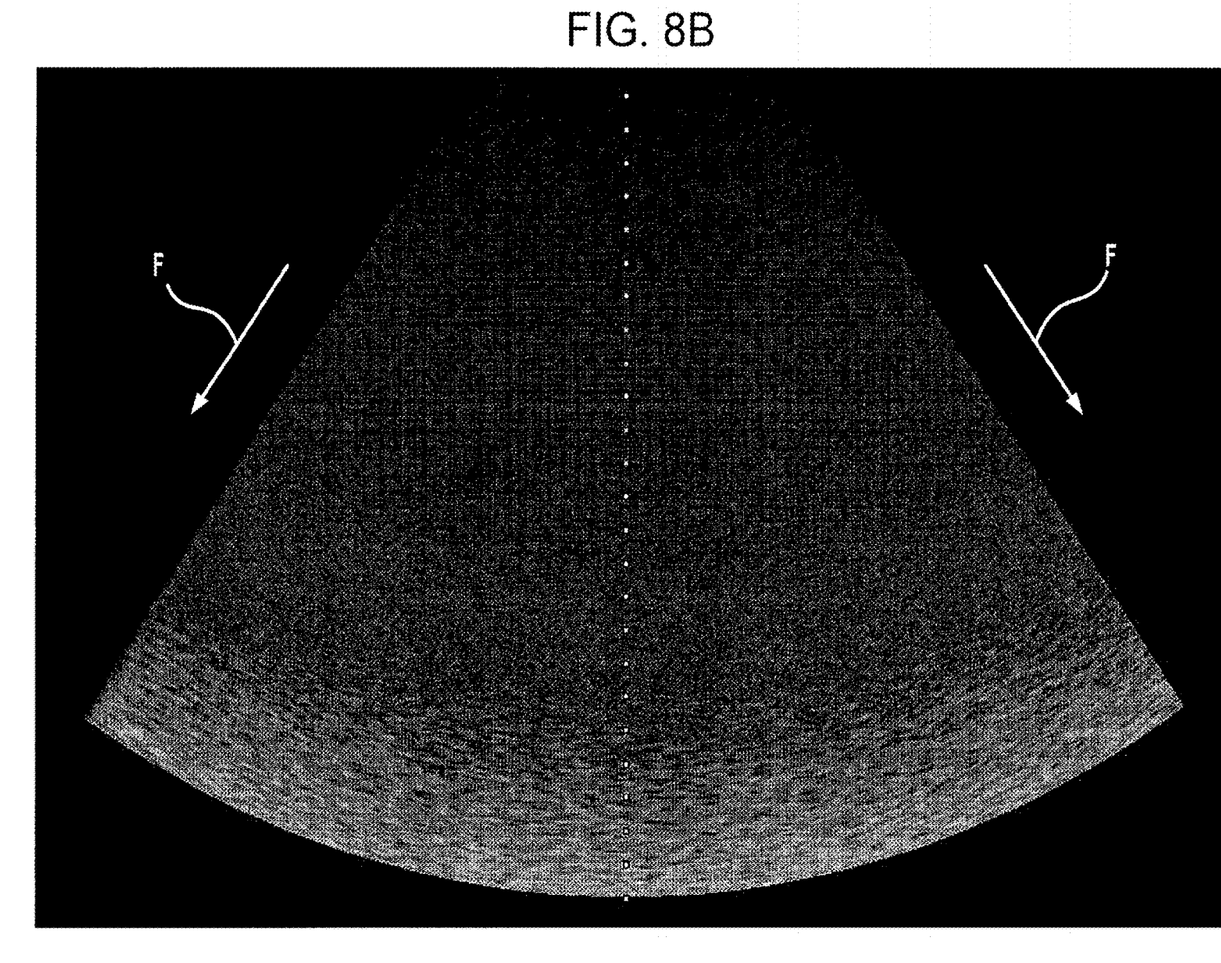
FIG. 8B is a diagram illustrating an example of an ultrasound image captured when the noise reduction is ON in the embodiment and the modification.

FIG. 8A is a diagram illustrating an example of an ultrasound image captured when the noise reduction is OFF in the embodiment and the modification. FIG. 8B is a diagram illustrating an example of an ultrasound image captured when the noise reduction is ON in the embodiment and the modification. In FIG. 8A, stripes rendered along the radial direction F of a fan-shaped ultrasound image represent an example of illustrated fixed noise. In an ultrasound image of FIG. 8B, the fixed noise is rendered by noise reduction. With the ultrasound image exemplified in FIG. 8B, from which the fixed noise has been reduced, the operator can perform diagnosis while viewing the ultrasound image. Thus, for example, it is possible to prevent the fixed noise from being misdiagnosed as a lesion.

With the ultrasound diagnosis apparatus and the medical image processing method according to at least one embodiment and the modification described above, after the noise data acquisition process, acquired noise data is used in common for corresponding scan lines. Thereby, it is possible to maintain the frame rate as well as reducing noise.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
   processing circuitry configured to:
   receive noise data with respect to each scan line by an ultrasound probe that is in a state that does not transmit ultrasound waves;
   acquire raster data with respect to each scan line by the ultrasound probe transmitting ultrasound waves with respect to each scan line, a frame of an ultrasound image data comprising the raster data corresponding to each of a plurality of scan lines; and
   subtract, from the raster data, the noise data corresponding to the scan line of the raster data over a plurality of frames, the noise data being repeatedly used over the plurality of frames.

2. The ultrasound diagnosis apparatus of claim 1, wherein the processing circuitry is further configured to
   generate different random noise data, and
   add the different random noise data to each piece of the noise data, and
   subtract the noise data, to which the random noise data has been added, from the raster data.

3. The ultrasound diagnosis apparatus of claim 2, wherein the processing circuitry is configured to:
   detect whether or not a predetermined condition has changed,
   receive new noise data upon detecting that the predetermined condition has changed, and
   subtract the new noise data from the raster data.

4. The ultrasound diagnosis apparatus of claim 3, wherein the processing circuitry is configured to detect whether or not the predetermined condition has changed after the subtracting, and the predetermined condition is at least one of decimation rate, gain, ultrasound probe, and receiving central frequency.

5. The ultrasound diagnosis apparatus of claim 4, wherein
the processing circuitry is configured to add a predetermined number of the noise data corresponding to the same scan line to obtain a sum data,
the number of the raster data to be combined for the same scan line is the predetermined number, and
the processing circuitry is further configured to subtract the sum data from the combined raster data.

6. The ultrasound diagnosis apparatus of claim 2, wherein
the processing circuitry is configured to add a predetermined number of the noise data corresponding to the same scan line to obtain a sum data,
the number of the raster data to be combined for the same scan line is the predetermined number, and
the processing circuitry is further configured to subtract the sum data from the combined raster data.

7. The ultrasound diagnosis apparatus of claim 3, wherein
the processing circuitry is configured to add a predetermined number of the noise data corresponding to the same scan line to obtain a sum data,
the number of the raster data to be combined for the same scan line is the predetermined number, and
the processing circuitry is further configured to subtract the sum data from the combined raster data.

8. The ultrasound diagnosis apparatus of claim 1, wherein
the processing circuitry is configured to:
    detect whether or not a predetermined condition has changed,
    receive new noise data upon detecting that the predetermined condition has changed, and
    subtract the new noise data from the raster data.

9. The ultrasound diagnosis apparatus of claim 8, wherein
the processing circuitry is configured to detect whether or not the predetermined condition has changed after the subtracting, and
the predetermined condition is at least one of decimation rate, gain, ultrasound probe, and receiving central frequency.

10. The ultrasound diagnosis apparatus of claim 9, wherein
the processing circuitry is configured to add a predetermined number of the noise data corresponding to the same scan line to obtain a sum data,
the number of the raster data to be combined for the same scan line is the predetermined number, and
the processing circuitry is further configured to subtract the sum data from the combined raster data.

11. The ultrasound diagnosis apparatus of claim 8, wherein
the processing circuitry is configured to add a predetermined number of the noise data corresponding to the same scan line to obtain a sum data,
the number of the raster data to be combined for the same scan line is the predetermined number, and
the processing circuitry is further configured to subtract the sum data from the combined raster data.

12. The ultrasound diagnosis apparatus of claim 1, wherein
the processing circuitry is configured to add a predetermined number of the noise data corresponding to the same scan line to obtain a sum data,
the number of the raster data to be combined for the same scan line is the predetermined number, and
the processing circuitry is further configured to subtract the sum data from the combined raster data.

13. A medical image processing method applicable to an ultrasound diagnosis apparatus, comprising:
    receiving noise data with respect to each scan line by an ultrasound probe that is in a state that does not transmit ultrasound wave;
    acquiring raster data with respect to each scan line by the ultrasound probe transmitting ultrasound waves with respect to each scan line , a frame of an ultrasound image data comprising the raster data corresponding to each of a plurality of scan lines; and
    subtracting, from raster data, the noise data corresponding to the scan line of the raster data over a plurality of frames, the noise data being repeatedly used over the plurality of frames.

* * * * *